(12) United States Patent
Neumann

(10) Patent No.: US 12,019,635 B2
(45) Date of Patent: *Jun. 25, 2024

(54) METHODS AND SYSTEMS FOR ARRANGING AND DISPLAYING GUIDED RECOMMENDATIONS VIA A GRAPHICAL USER INTERFACE BASED ON BIOLOGICAL EXTRACTION

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/963,573

(22) Filed: Oct. 11, 2022

(65) Prior Publication Data

US 2023/0031514 A1 Feb. 2, 2023

Related U.S. Application Data

(63) Continuation of application No. 17/062,740, filed on Oct. 5, 2020, now Pat. No. 11,544,275.

(51) Int. Cl.
*G06F 17/00* (2019.01)
*G06F 9/451* (2018.01)
(Continued)

(52) U.S. Cl.
CPC ........ *G06F 16/24575* (2019.01); *G06F 9/451* (2018.02); *G06F 16/24578* (2019.01);
(Continued)

(58) Field of Classification Search
CPC ......... G06F 16/24575; G06F 16/24578; G06F 16/248; G06F 16/285; G06F 9/451;
(Continued)

(56) References Cited

U.S. PATENT DOCUMENTS 7,953,613 B2   5/2011   Gizewski et al.
8,766,803 B2   7/2014   Bousamra et al.
(Continued)

OTHER PUBLICATIONS https://www.mdpi.com/2079-4991/9/6/813; Evolution of Wearable Devices with Real-Time Disease Monitoring for Personalized Healthcare; by: Guk, K.; Han, G.; Lim, J.; Jeong, K.; Kang, T.; Lim, E.-K.; Jung, J., (May 2019).

(Continued)

*Primary Examiner* — Greta L Robinson
(74) *Attorney, Agent, or Firm* — Caldwell Intellectual Property Law

(57) ABSTRACT

A system for arranging and displaying guided recommendations using a graphical user interface based on biological extraction, the system comprising a computing device configured to receive, from a wearable device located at a user, at least a biological extraction and at least a datum of user activity data, classify the biological extraction and the at least a datum of user activity as a function of at least a datum of a user fingerprint, select at least a compatible element as a function of the training data and the user fingerprint, wherein the compatible element comprises a guided recommendation, and generate a representation using a graphical user interface of the compatible element.

20 Claims, 8 Drawing Sheets

(51) Int. Cl.
  *G06F 16/2457* (2019.01)
  *G06F 16/248* (2019.01)
  *G06F 16/28* (2019.01)
  *G06N 5/04* (2023.01)
  *G06N 20/00* (2019.01)

(52) U.S. Cl.
  CPC .......... *G06F 16/248* (2019.01); *G06F 16/285* (2019.01); *G06N 5/04* (2013.01); *G06N 20/00* (2019.01)

(58) Field of Classification Search
  CPC .......... G06N 5/04; G06N 20/00; G06N 3/045; G06N 3/088; G16H 10/60
  See application file for complete search history.

(56) References Cited

U.S. PATENT DOCUMENTS

| | | | |
|---|---|---|---|
| 10,314,547 B2 | 6/2019 | Miller et al. | |
| 10,360,343 B2 | 7/2019 | Prakash et al. | |
| 10,368,810 B2 | 8/2019 | Quinn et al. | |
| 10,553,319 B1 | 2/2020 | Neumann | |
| 10,568,570 B1* | 2/2020 | Sherpa | G06N 3/084 |
| 11,461,700 B2* | 10/2022 | Neumann | G06F 3/011 |
| 11,544,275 B2* | 1/2023 | Neumann | G06N 3/045 |
| 2003/0036683 A1 | 2/2003 | Kehr et al. | |
| 2013/0218588 A1 | 8/2013 | Kehr et al. | |
| 2018/0113982 A1 | 4/2018 | Asthana et al. | |
| 2019/0295440 A1* | 9/2019 | Hadad | G06F 40/295 |
| 2020/0185100 A1 | 6/2020 | Francois et al. | |

OTHER PUBLICATIONS https://www.himss.org/resources/wearable-technology-applications-healthcare-literature-review; Wearable Technology Applications in Healthcare: A Literature Review; By: Min Wu, PhD and Jake Luo, PhD.

http://www.selectsmart.com/fitnesstracker/; Fitness Activity Tracker, (Dec. 2020).

* cited by examiner

METHODS AND SYSTEMS FOR ARRANGING AND DISPLAYING GUIDED RECOMMENDATIONS VIA A GRAPHICAL USER INTERFACE BASED ON BIOLOGICAL EXTRACTION

CROSS-REFERENCE TO RELATED APPLICATIONS

This application is a continuation of Non-provisional application Ser. No. 17/062,740, filed on Oct. 5, 2020, and entitled "METHODS AND SYSTEMS FOR ARRANGING AND DISPLAYING GUIDED RECOMMENDATIONS VIA A GRAPHICAL USER INTERFACE BASED ON BIOLOGICAL EXTRACTION," the entirety of which is incorporated herein by reference.

FIELD OF THE INVENTION

The present invention generally relates to the field of machine-learning. In particular, the present invention is directed to systems and methods for arranging and displaying guided recommendations using a graphical user interface based on biological extraction.

BACKGROUND

Physiological determinations generated are oftentimes cumbersome due to the volume of data associated with the output. Accurately and cleanly arranging and displaying the myriad of data associated with a user's physiology is a monumental task for graphical user interfaces, and especially so for guiding user recommendations as a function of the physiological data.

SUMMARY OF THE DISCLOSURE

In an aspect, a system for arranging and displaying guided recommendations via a graphical user interface based on biological extraction. The computing device is configured to receive at least a biological extraction and at least a datum of user activity data. The at least a datum of user activity data includes recent online purchases of the user. The computing device classifies the biological extraction and the at least a datum of user activity to at least a user fingerprint. Then the computing device selects a plurality of compatible elements as a function of the user fingerprint, wherein each of the plurality of compatible elements comprises a guided recommendation. The computing device then orders each compatible element of the plurality of compatible elements as a function of a compatibility index. The computing device displays a representation of the ordered compatible elements using a graphical user interface.

In another aspect, a method for arranging and displaying guided recommendations via a graphical user interface based on biological extraction, at least a biological extraction. The method also includes receiving, at the computing device, at least a datum of user activity data, wherein user activity data comprises recent online purchases of the user. The method then classifies, using the computing device, the biological extraction and the at least a datum of user activity to at least a user fingerprint. The method then selects, using the computing device, a plurality of compatible elements as a function of the user fingerprint, wherein each of the plurality of compatible elements comprises a guided recommendation. The method also includes ordering, using the computing device, each compatible element of the plurality of compatible elements as a function of a compatibility index. The method then displays, using the computing device, a representation of the ordered compatible elements using a graphical user interface These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for arranging and displaying guided recommendations using a graphical user interface based on biological extraction. In an embodiment, computing device is configured receive a biological extraction of a user from a variety of sources such as using user input such as a questionnaire and wearable device data such as a medical or fitness device. Computing device may be configured to classify biological extraction data and user activity data into a variety of subclassifications as a function of a user fingerprint. Computing device may display, using a graphical user interface, a compatible element containing a guided recommendation, wherein recommendations are guided in that they are filtered as a function of user patterns and targeted to user based on wearable device data.

At a high level, aspects of the present disclosure are directed to system and methods for arranging and displaying guided recommendations using a graphical user interface (GUI) based on biological extraction derived from wearable device data. In an embodiment, an evolving GUI may display targeted (guided) representations based on physiological data that originates from a wearable device, as defined herein. Wearable device data may be used as training data to train machine-learning models to match to the data to a category of biological extraction, as described herein, and weigh the category for relevancy in matching to a user's internet usage of computing devices (activity data). In an embodiment, a compatibility index can be calculated and use to filer (weight/rank) the targeted (guided) recommendations and generate a user-customized GUI representation.

Figure 1:
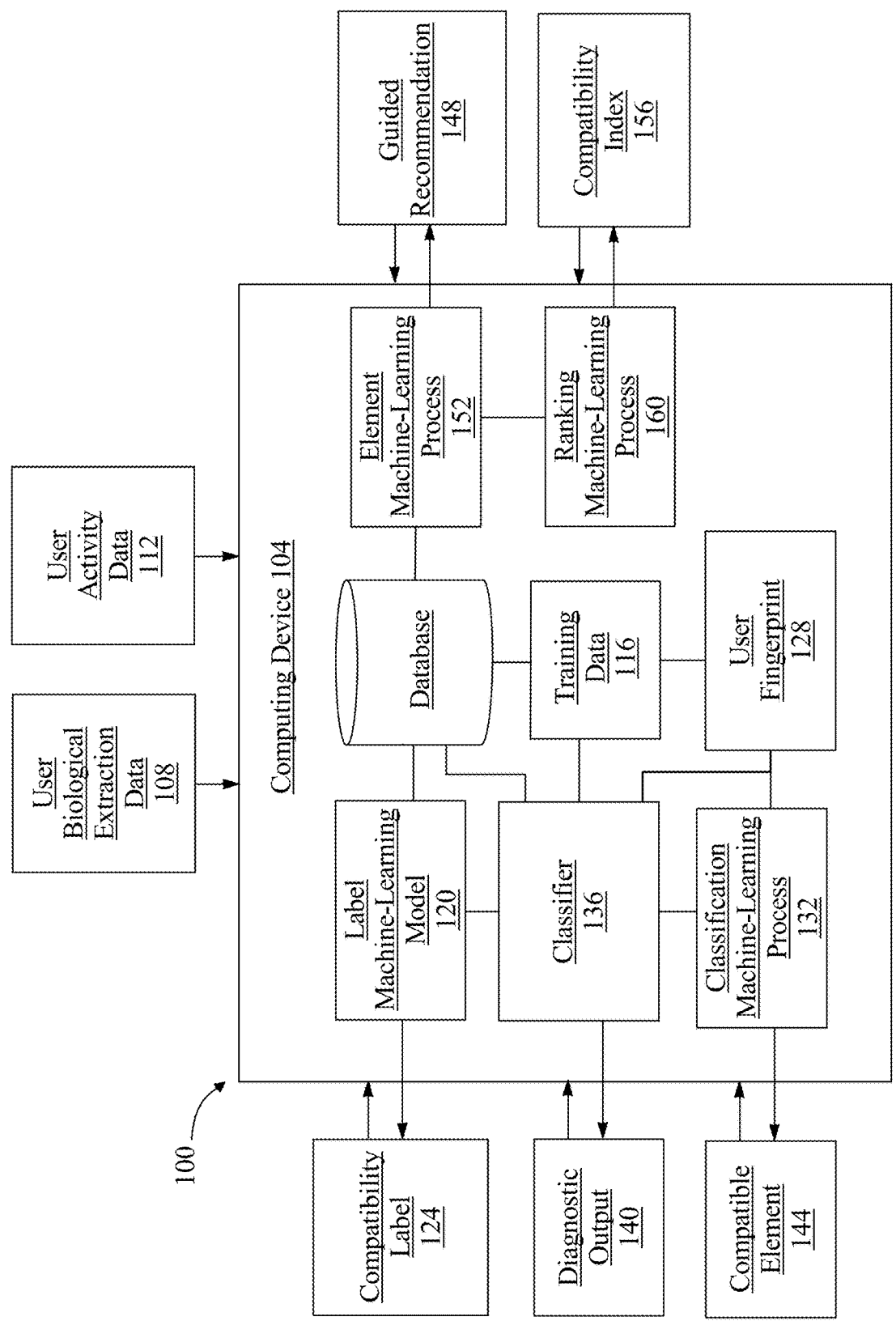
FIG. 1 is a block diagram illustrating a system of arranging and displaying guided recommendations using a graphical user interface based on biological extraction.

Referring now to FIG. 1, an exemplary embodiment of a system 100 for arranging and displaying information on a graphical user interface based on a biological extraction is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail using a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing in reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is configured to receive, from a wearable device located at a user, at least a biological extraction of a user. A "biological extraction," as used in this disclosure, is any biological, chemical, physiological, medical, genetic, behavioral, psychological, and the like, data that is associated with a user, including past data, currently-generated data, and simulated and/or predicted future data. Biological extraction 108 data may include medical histories, diseases, surgeries, injuries, symptoms, exercise frequency, sleep patterns, lifestyle habits, and the like, that may be used to inform a user's lifestyle, including diet, and the like. Biological extraction 108 data may include diet information such as nutrition deficiencies, food intolerances, allergies, and the like. Biological extraction 108 data may be provided by a second individual on behalf of a user, for instance and without limitation a physician, medical professional, nurse, hospice care worker, mental health professional, and the like. Biological extraction 108 may alternatively or additionally include a plurality of dimensions of biological extraction 108 data any data used as a biological extraction as described in U.S. Nonprovisional application Ser. No. 16/886,647, filed on May 28, 2020, and entitled "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, A "wearable device," as used in this disclosure, is a device on the person of a user that collects biological extraction data about the user, where "on the person" indicates that the device is portable and is either worn on the user, inside the user, in contact with user, or in close proximity to the user. Biological extraction 108 may include data generated, collected, and/or transmitted by a wearable device 108 and may include wearables worn by the by user such as an accelerometer, pedometer, gyroscope, fitness trackers, force monitors, motion sensors; wearables in contact with a user's skin such as in electrocardiography (ECG), electrooculography (EOG), bioimpedance, blood pressure and heart rate monitoring, oxygenation data, biosensors; wearables that may be placed inside and/or within a user, for instance, beneath the skin, such as pacemakers, capsule cameras, biosensors, endoscopes, and the like; and/or devices that may be adapted to be placed outside of the user but aimed at collecting data pertaining to the user, such as audio-visual capture, social media platform data, magnetic resonance imaging (MM), X-ray imaging, facial recognition, and the like. Wearable devices may be any devices capably and useful in acquiring, measuring, and/or transmitting biometrics—body measurements and calculates related to human characteristics. Biometric data may include any data that is useful in biometrically identifying a user, including fingerprints, retina scans, genetic material data, physical appearance, voice recognition, or any other data useful in identifying an individual.

Continuing in reference to FIG. 1, computing device 104 is configured to receive at least a datum of user activity data, wherein user activity data may include data collected via user input through a graphical user interface. As used in this disclosure, "user activity data," is data that relates to user activity while using a computing device 104, including any user input. As used in this disclosure, a "user input," is an element of user-derived information that is intended to communicate with computing device 104 via an interface. User activity data 112 may include user input regarding online shopping, web browser data, social media use, recent purchases, and the like, that may be useful in curating and/or improving a graphical user interface display. A "graphical user interface," as used in this disclosure, is any form of a user interface that allows a user to interface with an electronic device through graphical icons and displays, audio indicators, text-based interface, typed command labels, text navigation, and the like, wherein the interface is configured to provide information to the user and accept input from the user.

Continuing in reference to FIG. 1, receiving, from a wearable device located at a user, at least a biological extraction and at least a datum of user activity data may include generating, using the wearable device data, a first training set including a plurality of first data entries including at least an element of wearable device data correlated to at least an element of biological extraction. "Training data," as used herein, is data containing correlations that a machine-learning process may use to model relationships between two or more categories of data elements, as described in further detail below. For instance, and without limitation, training data 116 may include a plurality of data entries, each entry representing a set of data elements that were recorded, received, and/or generated together; data elements may be correlated by shared existence in a given data entry, by proximity in a given data entry, or the like. Multiple data entries in training data 116 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 116 according to various correlations; correlations may indicate causative and/or predictive links between categories of data elements, which may be modeled as relationships such as mathematical relationships by machine-learning processes as described in further detail below. Training data 116 may be formatted and/or organized by categories of data elements, for instance by associating data elements with one or more descriptors corresponding to categories of data elements. As a non-limiting example, training data 116 may include data entered in standardized forms by persons or processes, such that entry of a given data element in a given field in a form may be mapped to one or more descriptors of categories. Elements in training data 116 may be linked to descriptors of categories by tags, tokens, or other data elements; for instance, and without limitation, training data 116 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 1, training data 116 may include one or more elements that are not categorized; that is, training data 116 may not be formatted or contain descriptors for some elements of data. Machine-learning algorithms and/or other processes may sort training data 116 according to one or more categorizations using, for instance, natural language processing algorithms, tokenization, detection of correlated values in raw data and the like; categories may be generated using correlation and/or other processing algorithms, as described in further detail below. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 180 to be made applicable for two or more distinct machine-learning algorithms as described in further detail herein. Training data 116 used by machine-learning module may correlate any input data as described in this disclosure to any output data as described in this disclosure, as described in further detail below.

Further referring to FIG. 1, training data 116 may be filtered, sorted, and/or selected using one or more supervised and/or unsupervised machine-learning processes and/or models as described in further detail below; such models may include without limitation a training data classifier, as described in further detail below. In non-limiting exemplary embodiments, wearable device data may include organization into training data 116 sets for determinations described herein, wherein wearable device data may be a set of signals, for instance from a biosensor, wherein the signals may be correlated to at least an element of biological extraction such as blood pressure during exercise. Alternatively or additionally, wearable device data may include biometrics that may be useful in generating training data 116 that may train a machine-learning model for an outputting a biometric identification of a user. Activity data 112 may include organization into training data 116 sets for determinations described herein.

Continuing in reference to FIG. 1, receiving at least a biological extraction 108 may include training a label machine-learning model using training data, wherein training data includes a plurality of data entries, each data entry of the plurality of data entries including at least an element of biological extraction 108 data correlated to a user function, and generating, using the label machine-learning model, a compatibility label. A label machine-learning model 120 may be generated by a computing device 104 performing a machine-learning algorithm and/or process by using a machine-learning module, as described in further detail below. Training data 116 may originate from the wearable device data present in a user's biological extraction 108, as described above, for instance user ECG/EKG signals as a function of time wherein the training data 116 may relate to user functions such as deep sleep, light sleep, rapid eye movement (REM) sleep, and states of being awake.

Continuing in reference to FIG. 1, a "compatibility label," as used in this disclosure, is an identifier that relates biological extraction data 108 to a user function such as exercise, sleep, and the like, wherein the compatibility label contains qualitative and/or quantitative data that relates how accurate the biological extraction relate to the user function, the nature of the user function, among other data. A compatibility label 124 may include, for instance and without limitation, a variety of leisure activities such as biking, swimming, hiking, and the like, mapped to wearable device data such as a pedometer, gyroscope, accelerometer, bioimpedance, and the like, wherein the compatible level 124 may also include a quantitative metrics that relates how well the wearable device data maps to the activity. For instance, and without limitation, a compatibility label 124 may qualitative data that indicates a category of user function as 'running' and may further include quantitative data depicting a 75% certainty that the wearable device data illustrates a user is running. In such an example, compatibility label 124 may also include additional quantitative data that relates the amount of running in distance, time, the frequency of engaging in running, the level of mastery of running, and the like.

Continuing in reference to FIG. 1, computing device 104 is configured to classify the biological extraction 108 and the at least a datum of user activity to at least a datum of a user fingerprint. A "user fingerprint," is a file generated by system 100 that encompasses all biological extraction 108 and user activity data 112. For instance, and without limitation, a user fingerprint 128 may include data concerning wearable device data and biological extraction 108 determined from the wearable device data. In non-limiting illustrative examples, user fingerprint 128 may include activity data 112 such as a user's propensity to run and may include a recent purchase of running shoes and/or running apparel; user fingerprint 128 may be referred to by computing device 104 to generate 'guide recommendations' directed toward something other than running shoes and/or apparel, but that still matches the interests of a person who enjoys running. A user fingerprint 128 may be used by system 100 to identify redundancies in what is displayed using a GUI so that those redundancies can be filtered, as described in further detail below. A user fingerprint 128 may be used by system 100 to identify gaps, or GUI-displayable elements that have not been presented to a user before, as described in further detail below. Biological extraction data 108 and user activity data 112 may be classified into subsets of data to generate a user fingerprint 128, for instance and without limitation, as described in U.S. Nonprovisional application Ser. No. 16/532,283, filed on Aug. 5, 2019, and entitled "METHODS AND SYSTEMS FOR USING ARTIFICIAL INTELLIGENCE TO ANALYZE USER ACTIVITY DATA," the entirety of which is incorporated herein by reference.

Continuing in reference to FIG. 1, classifying the biological extraction 108 and the at least a datum of user activity may include using a classification machine-learning process to generate a classifier. A classification machine-learning process 132 may include any machine-learning algorithm and/or process performed by using a machine-learning module, as described in further detail below. A "classifier," as used in this disclosure, is configured to output at least a datum that labels or otherwise identifies a set of data that are clustered together, as described in further detail below. A classifier 136 may represent a body of data that is a series of compatibility labels 124 from a plurality of users associated with diagnostic outputs. In non-limiting illustrative examples, a classifier 136 may relate to activity data, web-browsing patterns, purchasing patterns, interests, wearable device data, biological extraction, or the like, that may be a packet of data used to search or otherwise identify a user fingerprint 128, diagnostic output, guided recommendation, or any other determination output by system 100 as described herein.

Continuing in reference to FIG. 1, a classifier 136 may describe a subset of diagnostic outputs. A "diagnostic output," as used in this disclosure, is a subset of biological extraction 108 and/or user activity data 112 as a function of past user data contained in the user fingerprint 128. In non-limiting illustrative examples, diagnostic output 140 may include, for instance, a cache of user browsing history that relates to shopping for objects associated with a compatibility label 124. In such an example, a classifier 136 may contain diagnostic outputs 140 describing a plurality of compatibility labels 124 from a plurality of alike users, wherein such a classifier 136 may help improve the full spectrum and accuracy of 'guided recommendations' as it relates to, for instance, purchasing. In further non-limiting illustrative examples, a diagnostic output 140 may concern how compatibility labels 124 corresponds to user activity data 112—i.e. how do compatible labels 124 relate to how a user spends their time, money, internet usage, and the like. In this way, a diagnostic output 140 may be used by system 100 to more accurately match how "willing" a user may be to spend money on an object based on how often they engage in an activity relating to the object. Furthermore, using a classification machine-learning process 132 to generate classifiers 136 may increase the robustness of any one diagnostic output 140. Classification machine-learning process 132 may accept biological extraction 108 and user activity data 112 and generate a classifier 136 that assigns categorical class labels to subsets of the biological extraction data 108 as it may relate, match, or otherwise be categorized with user activity data 112. Such classifications and classifiers, along with the associated categorized data may be stored in the user fingerprint 128.

Continuing in reference to FIG. 1, computing device 104 is configured to select at least a compatible element as a function of the training data and the user fingerprint 128, wherein the compatible element comprises a guided recommendation. A "compatible element," as used in this disclosure, is a packet of data the GUI will receive to 'know' what should be displayed, including the order, what the elements are, and how they are connected to wearable BE, past user experience, and/or any other data contained in the user fingerprint 128, biological extraction 108, training data, and the like. A "guided recommendation," as used in this disclosure is an output that directs a GUI to retrieve and display a recommended internet-based activity relating to the classifier 136. For instance and without limitation, a classifier 136 may describe a subset of diagnostic outputs 140 concerning "running", wherein the guided recommendation 148 instructs a GUI to point user toward shopping for running apparel, running shoes, locating and signing up for a local running club, a running blog, the Boston marathon, purchasing a stationary bike, engaging in other aerobic exercises, using other wearables, etc. In such an instance, guided recommendation 148 may include a packet of data concerning the content to be display by the GUI, the chronology (including the time to display, how it should change over time, what to display each time a user leaves and returns to GUI, etc.), etc. Guided recommendation 148 may include hyperlinked sources, for instance and without limitation, to websites via the internet, documents, mobile applications, games, messaging conversations, emailing, and the like. Guided recommendation 148 may instruct a GUI to display, connect with, or otherwise support any application or function available to a computing device 104 such as a "smartphone", laptop, tablet, internet-of-things (IOT) device, vehicle display, and the like.

Continuing in reference to FIG. 1, selecting a compatible element 144 may include using an element machine-learning process to select the compatible element as a function of the classifier 136. An element machine-learning process 152 may include any machine-learning algorithm and/or process performed by using a machine-learning module, as described in further detail below. Selecting at least a compatible element 144 may refer to selecting from at least a data record with a particular association, as described above, within the training data. For instance, such an association may be described by a classifier 136, as described herein. In non-limiting illustrative examples, an element machine-learning process 152 may accept an input that is a plurality of compatible elements 144, and may select at least a compatible element 144 from the plurality as a function of a classifier 136, wherein the compatible element 144 most supported by a classifier 136 may be selected. Element machine-learning process 152 may select compatible element 144 based on a criterion contained in a particular classifier 136, for instance and without limitation, a describing biological data that directly relates to recent shopping as it relates to the user.

Continuing in reference to FIG. 1, selecting a compatible element 144 using the element machine-learning process 152 may include generating the guided recommendation 148. Element machine-learning process 152 may accept an input that is a compatible element 144 and then generate an output that is a guided recommendation 148 based on the data contained in the compatible element 144. In non-limiting illustrative examples, a compatible element 144 may include a guided recommendation 148 concerning a customizable element of data to be displayed to a user using the GUI, wherein a guided recommendation 148 may be a user-input-compatible image to a specific purchasable object a user has a high expectation to buy based on wearable device data and biometrics.

Continuing in reference to FIG. 1, selecting the compatible element 144 may include using the element machine-learning process 152 to filter the guided recommendation 148 as a function the user fingerprint 128. Element machine-learning process 152 may accept an input that is a plurality of generated guided recommendations 148 and filter the guided recommendations 148 as a function of the user data contained in the user fingerprint 128, and generate a single, targeted guided recommendation 148. For instance, and without recommendation, element machine-learning process 152 may filter corresponding to the guided recommendation 148 which is most supported by wearable device data contained in the user fingerprint 128. Alternatively or additionally, element machine-learning process 152 may filter guided recommendations 148 based on recent purchases as logged in the activity data 112 in the user fingerprint 128. In such an example, a user may have recently purchased a first object, which may guide element machine-learning process 152 to 'filter out' guided recommendations 148 in a GUI that guide a user to purchasing a first object, and instead element machine-learning process 152 may output a guided recommendation 148 that is most closely associated with the 'filtered out' guided recommendations 148. Element machine-learning process 152 may accomplish that by selecting based off of training data sets, classifiers 136, or the like, as described above, which may describe data contained in user fingerprint 128.

Continuing in reference to FIG. 1, selecting the compatible element 144 as a function of filtering the guided recommendation 128 may include ranking, using a ranking machine learning process, guided recommendations 148 as a function of a compatibility index. Determining which guided recommendations 148 to filter may be determined by using a compatibility index. A "compatibility index," as used in this disclosure, is a qualitative and/or quantitative metric which measures the compatibility of a guided recommendation 148 for a user. Compatibility index 156 may include qualitative data such as a determination of 'include' and/or 'not include'. Compatibility index 156 may include quantitative data such as a numerical value that measures the 'compatibility with the user', 'likeliness to respond', and the like. Compatibility index 156 may include a score and/or ranking, as determined by a ranking machine-learning process 160. Ranking machine-learning process 160 may include any machine-learning algorithm and/or process performed by using a machine-learning module, as described in further detail below. Ranking machine-learning process 160 may rank each guided recommendation 148 as a function of data contained in user fingerprint 128. For instance, and without limitation, ranking machine-learning process 160 may highly rank the guided recommendation 148 that most closely resembles activities corresponding to user wearable device data.

Continuing in reference to FIG. 1, ranking machine-learning process 160 may assist element machine-learning process 152 in filtering out guided recommendations based on compatibility index 156. A "compatibility index," as used in this disclosure is a qualitative and/or quantitative metric relating to the compatibility a GUI-displayable element may have for the GUI. In non-limiting illustrative examples, compatibility index 156 may represent an index about a 'threshold value' that element machine-learning process 152 may accept as an input value for "making the decision" to send elements to the GUI for presentation, what order the elements should be in, the chronology of elements, etc. Elements may be for instance guided recommendations 148, including text, images, audio-visual elements, hyperlinked elements, and the like. For instance and without limitation, each time a user opens the GUI, and reopens later, different elements may be displayed, the order of elements may change, etc., based on the ranking of elements based on the compatibility index 156. Compatibility index 156 may represent a ranking in a list, such as a queue, so that once a user has selected an element and/or acted upon an element, the queue may dictate what is to be displayed next based on compatibility index 156.

Continuing in reference to FIG. 1, computing device 104 is configured to generate a representation using a graphical user interface of the compatible element 144. Computing device 104 may generate a representation of the compatible element 144 using a graphical user interface, as described herein. Computing device 104 may generate a display using a user device, such as a "smartphone", laptop, tablet, internet-of-things (JOT) device, vehicle display, and the like.

Continuing in reference to FIG. 1, generating a representation using a graphical user interface of the compatible label may include updating the graphical user interface display as a function of the compatibility index 156. Computing device 104 may update generated representations using the graphical user interface. As used herein, "update," may refer to any alteration, modification, and/or change in GUI appearance, display, generated representations, related to compatible element 144, guided recommendations 148, of generating representations of any of the outputs described herein. In non-limiting illustrative examples, computing device 104 may alter, change, or otherwise update GUI as a function of the compatibility index 156. Computing device 104 may alter, change, or otherwise update GUI as a function of user activity data 112, wearable device data, and/or user fingerprint 128.

Figure 2:
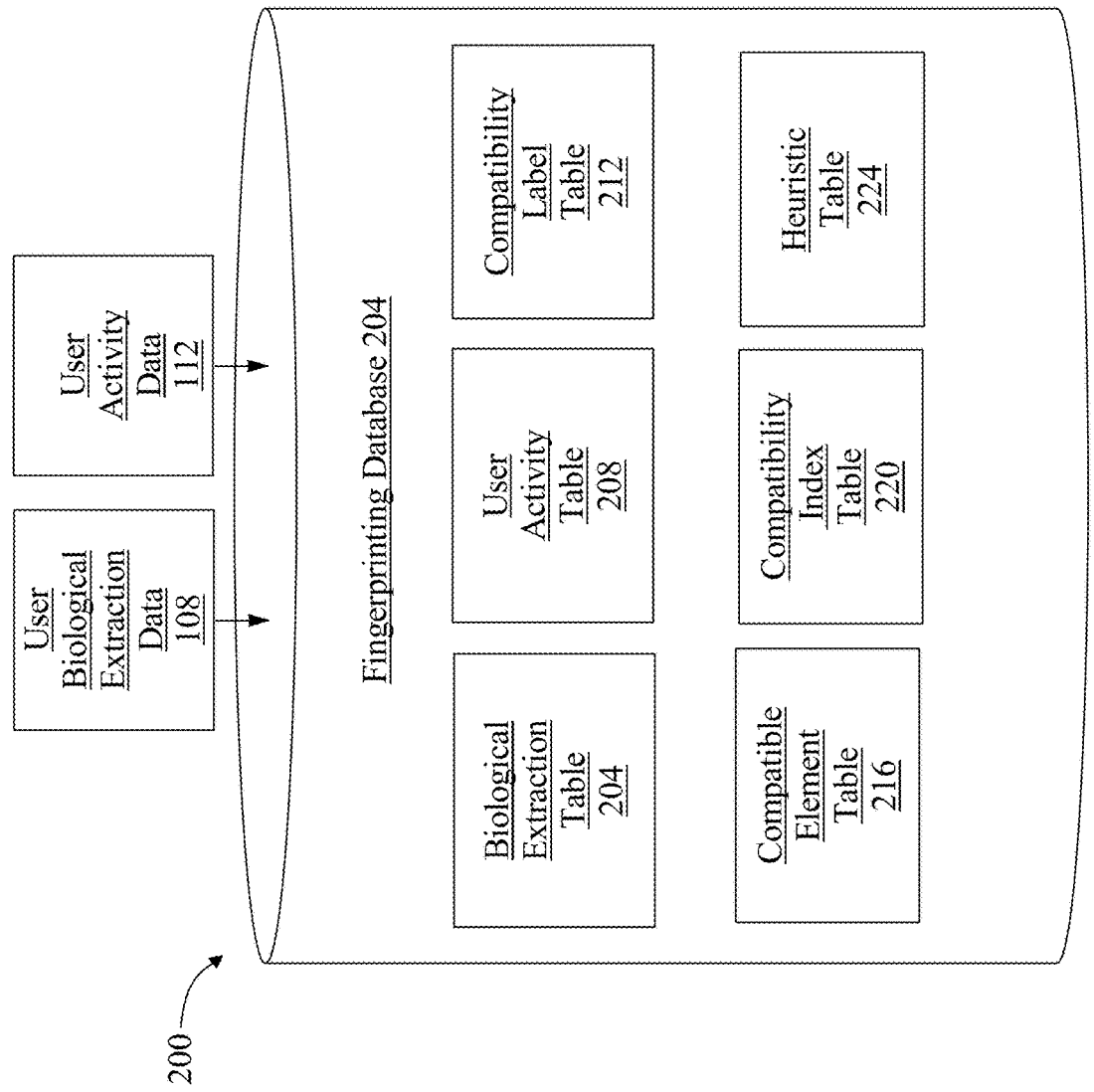
FIG. 2 is a block diagram illustrating a non-limiting exemplary embodiment of a fingerprint database.

Referring now to FIG. 2, a non-limiting exemplary embodiment 200 of a fingerprint database 204 is illustrated. A fingerprint database 204 may be used by computing device 104 to store and/or retrieve inputs and outputs as described herein, user-specific data such as biological extraction 208 data, wearable device data, user activity data 112, and/or any determinations made by a machine-learning process, model, and/or algorithm, as described herein. Fingerprint database 204 may be implemented, without limitation, as a relational database, a key-value retrieval database such as a NOSQL database, or any other format or structure for use as a database that a person skilled in the art would recognize as suitable upon review of the entirety of this disclosure. Fingerprint database 204 may alternatively or additionally be implemented using a distributed data storage protocol and/or data structure, such as a distributed hash table and the like. Fingerprint database 204 may include a plurality of data entries and/or records, as described herein. Data entries in a Fingerprint database 204 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 3:
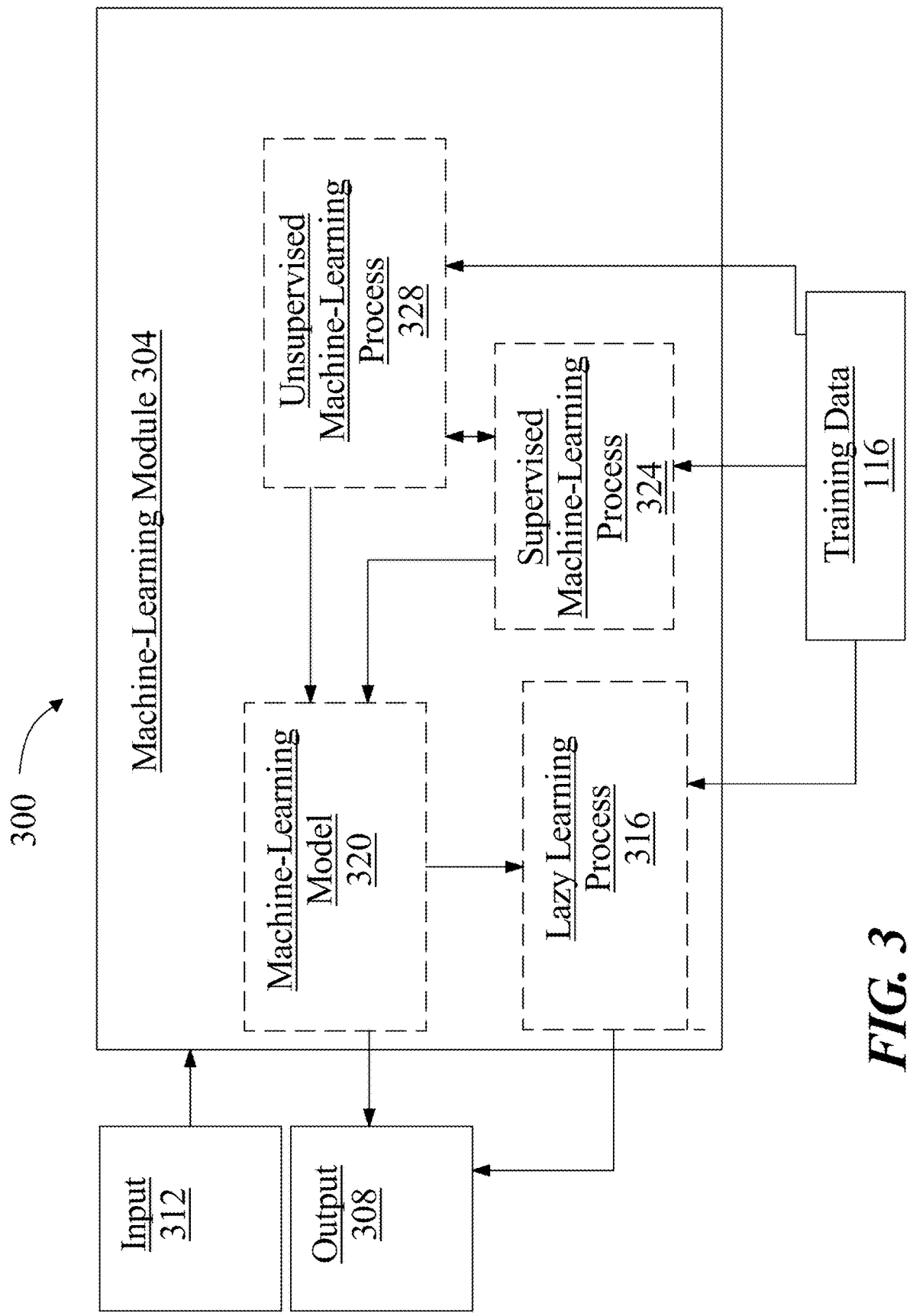
FIG. 3 is a block diagram of a non-limiting exemplary embodiment of a machine-learning module.

Further referring to FIG. 3, Fingerprint database 204 may include, without limitation, a biological extraction table 204, user activity table 208, compatibility label table 212, compatible element table 216, compatibility index table 220, and/or heuristic table 224. Determinations by a machine-learning process, machine-learning model, ranking function, and the like, may also be stored and/or retrieved from the Fingerprint database 204, for instance in non-limiting examples a classifier 136 describing a plurality of biological extraction 108 as it relates to a plurality guided recommendations 148, wherein a classifier 136 is an identifier that denotes a subset of data that contains a heuristic and/or relationship, as may be useful to system 100 described herein. As a non-limiting example, Fingerprint database 204 may organize data according to one or more instruction tables. One or more Fingerprint database 204 tables may be linked to one another by, for instance in a non-limiting example, common column values. For instance, a common column between two tables of Fingerprint database 204 may include an identifier of a submission, such as a form entry, textual submission, global position system (GPS) coordinates, addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of an Fingerprint database 204 may include, as a non-limiting example, a biological extraction table 204, which may include categorized biological extraction 108 data, as described above, including biological, physiological, chemical, genetic, medical histories, diseases, etc., originating from, for instance, a wearable device. One or more tables may include user activity table 208, which may include a user activity data 112 that a system 100 may use to generate compatibility labels 124, diagnostic output 140, compatible elements 144, guided recommendations 148, and the like, for instance and without limitation. One or more tables may include compatibility label table 212, which may include classifiers, data, and the like, for instance and without limitation, that system 100 may use to retrieve and/or generate compatibility labels 212, associated with user. One or more tables may include compatible element table 216, which may include compatibility elements 144, including, generated recommendations 148, classifiers, data, and the like, for instance and without limitation, that system 100 may use to retrieve and/or store compatibility elements 144, associated with user. One of more tables may include a compatibility index table 220, which may include a plurality of compatibility elements 144, guided recommendations 148, and the like, in a queue, list, or ranking, according to compatibility index 156; compatible element table 216 may include ranking machine-learning process 160 outputs, determinations, variables, and the like, organized into subsets of data. One or more tables may include, without limitation, a heuristic table 328, which may organize rankings, indexes, models, outcomes, functions, numerical values, vectors, matrices, and the like, that represent determinations, optimizations, iterations, limitations, rankings, variables, and the like, including one or more inputs describing potential mathematical relationships, as described herein. For instance, and without limitation, heuristic table 328 may contain classifiers 136 related to subsets of training data 116 and associated models, such as label machine-learning model 120.

Referring now to FIG. 3, an exemplary embodiment 300 of a machine-learning module 304 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 116 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, machine-learning module 304 may be configured to perform a lazy-learning process 316 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 116. Heuristic may include selecting some number of highest-ranking associations and/or training data 116 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 3, machine-learning processes as described in this disclosure may be used to generate machine-learning models 320. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 320 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 320 may be generated by creating an artificial neural network, such as a convolutional neural network comprising an input layer of nodes, one or more intermediate layers, and an output layer of nodes. Connections between nodes may be created via the process of "training" the network, in which elements from a training data 116 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 324. At least a supervised machine-learning process 324, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an element machine-learning process 152, wherein the supervised learning algorithm may accept a plurality of compatible elements 144 as described above as inputs, guided recommendations 148 as outputs, and a ranking function representing a desired form of relationship to be detected between inputs and outputs; ranking function may, for instance, seek to maximize the probability that a given input and/or combination of elements inputs is associated with a given output to minimize the probability that a given input is not associated with a given output. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 116. For instance and without limitation, a ranking machine-learning process 160 may include a supervised machine-learning process, wherein the ranking machine-learning process 160 accepts an input of a plurality of guided recommendations and executes a ranking function representing a desired form of relationship to be detected between inputs and outputs, resulted in an output of a compatibility index 156 for the inputs. Persons skilled in the art, upon reviewing the entirety of this disclosure, will be aware of various possible variations of at least a supervised machine-learning process 324 that may be used to determine relation between inputs and outputs. Supervised machine-learning processes may include classification algorithms as defined above.

Further referring to FIG. 3, machine learning processes may include at least an unsupervised machine-learning processes 328. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 304 may be designed and configured to create a machine-learning model 320 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 116 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 116.

Figure 4:
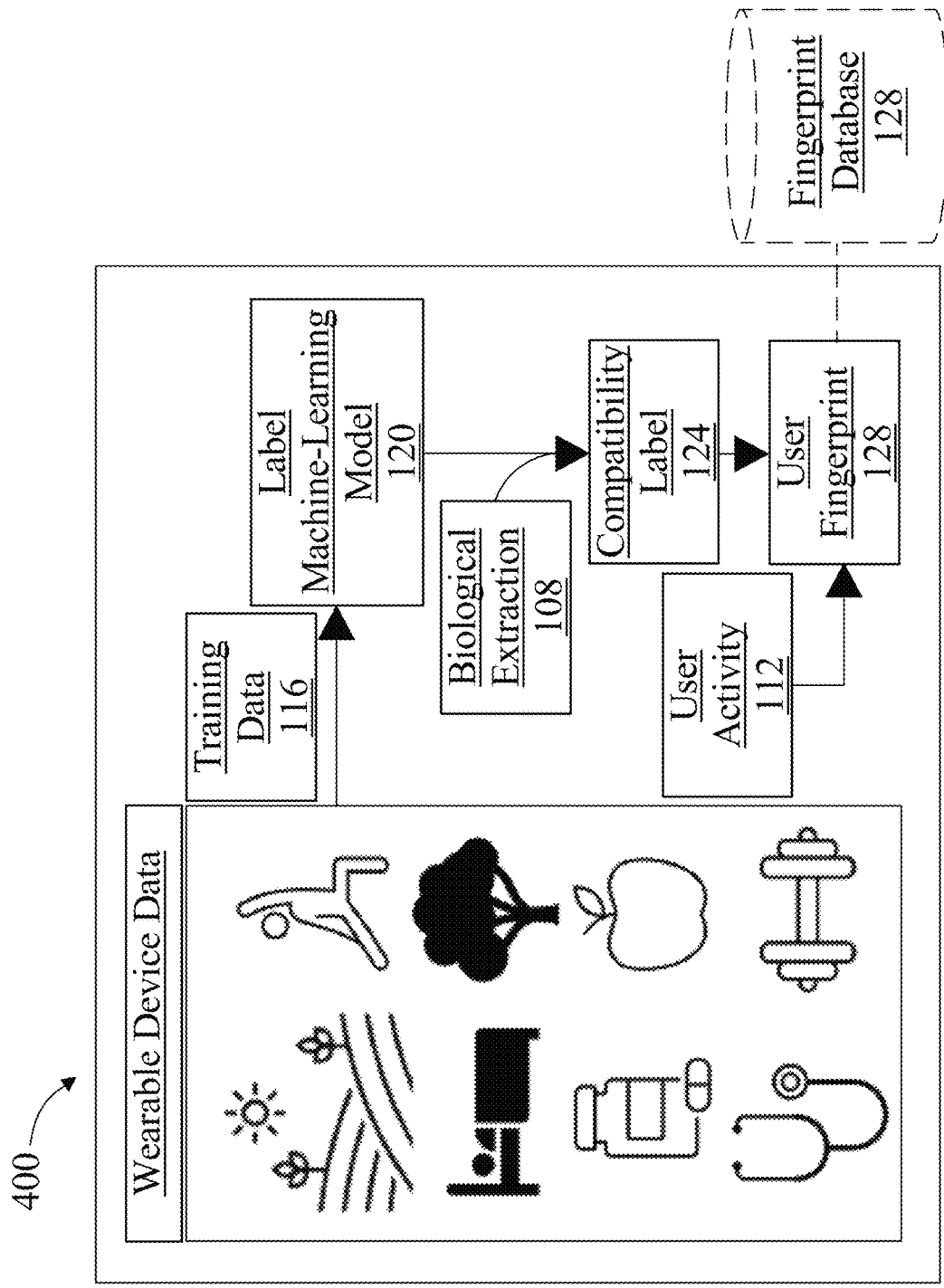
FIG. 4 is block diagram illustrating a non-limiting exemplary embodiment of a user fingerprint.

Referring now to FIG. 4, a non-limiting exemplary embodiment 400 of a user fingerprint 128 is illustrated. System 100 may accept wearable device data originating from a variety of categories, such as health, fitness, sleep, nutrition, exercise, medical history, current supplementation and medications, mental health, and the like, and generate training data 116 from the wearable device data. Computing device 104 may train label machine-learning model 120 with training data 116 to generate an output of compatibility label 124. User fingerprint 128 may include compatibility label 124 and user activity data 112 for generating a diagnostic output 140. User fingerprint 128 data may be stored and/or retrieved from a fingerprint database 304, as described above.

Figure 5:
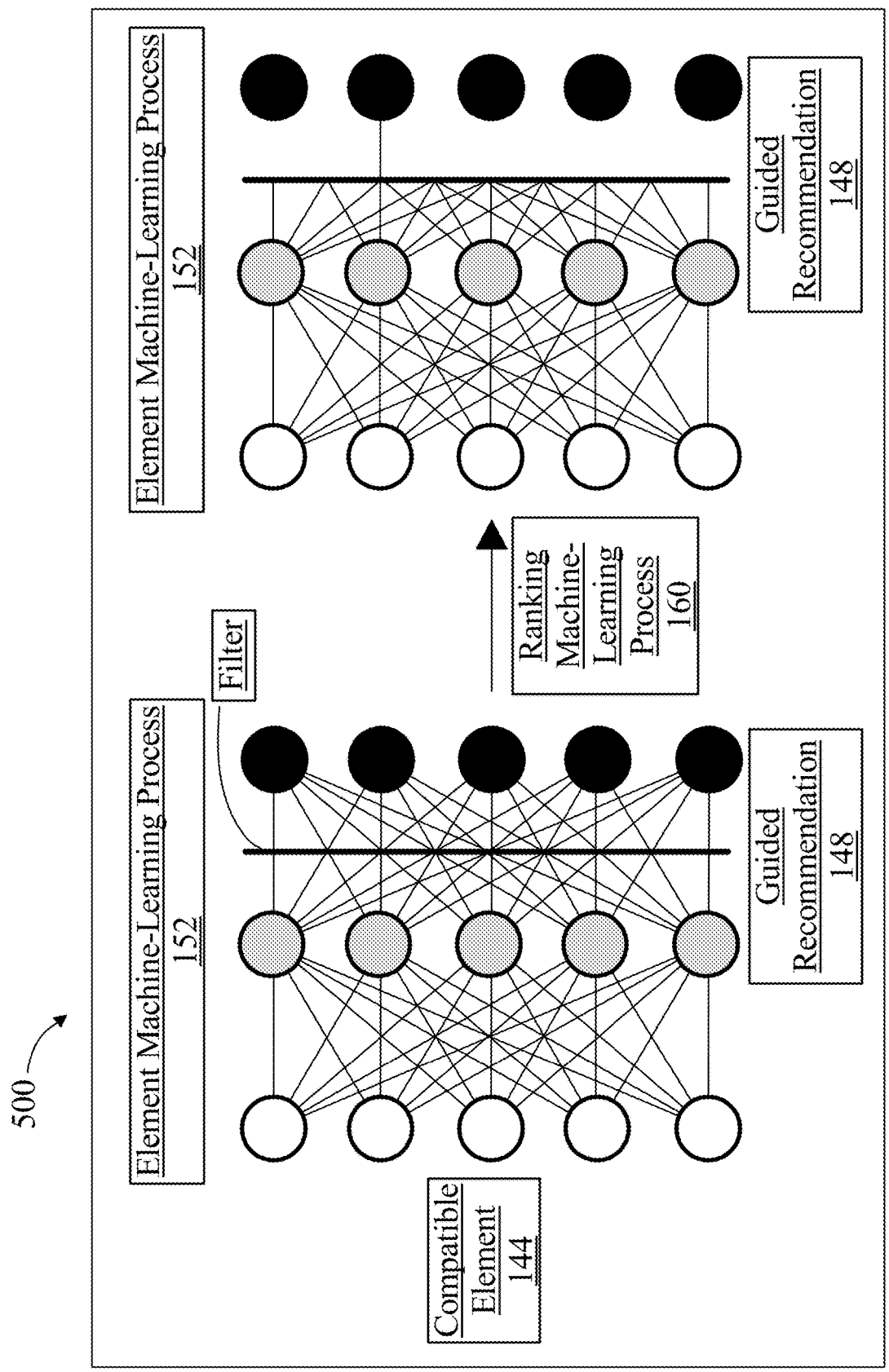
FIG. 5 is a diagrammatic representation illustrating a non-limiting exemplary embodiment of an element machine-learning learning process.

Referring now to FIG. 5, a non-limiting exemplary embodiment of an element machine-learning learning process 152 is illustrated. Element machine-learning process 152 may accept an input of a plurality of compatible elements 144 (denoted as white circles) and generate an output that is a plurality of guided recommendations 148 (denoted as grey circles). Element machine-learning process 152 may generate the same guided recommendation 148 for one or more compatible elements 144; likewise, element machine-learning process 152 may generate more than one guided recommendation 148 for a single compatible element 144. Element machine-learning process 152 may filter guided recommendations 148 using a variety of criteria. For instance and without limitation, ranking machine-learning process 160 may accept an input of a plurality of guided recommendations 148, and associated data, and generate an output that is a ranking of the plurality of guided recommendations 148, wherein the ranking comprises a compatibility index 156. Element machine-learning process 152 may retrieve a plurality of compatibility indexes 156 associated with a plurality of guided recommendations 148 and filter based on the compatibility indexes 156 (as depicted on the right of FIG. 5).

Figure 6:
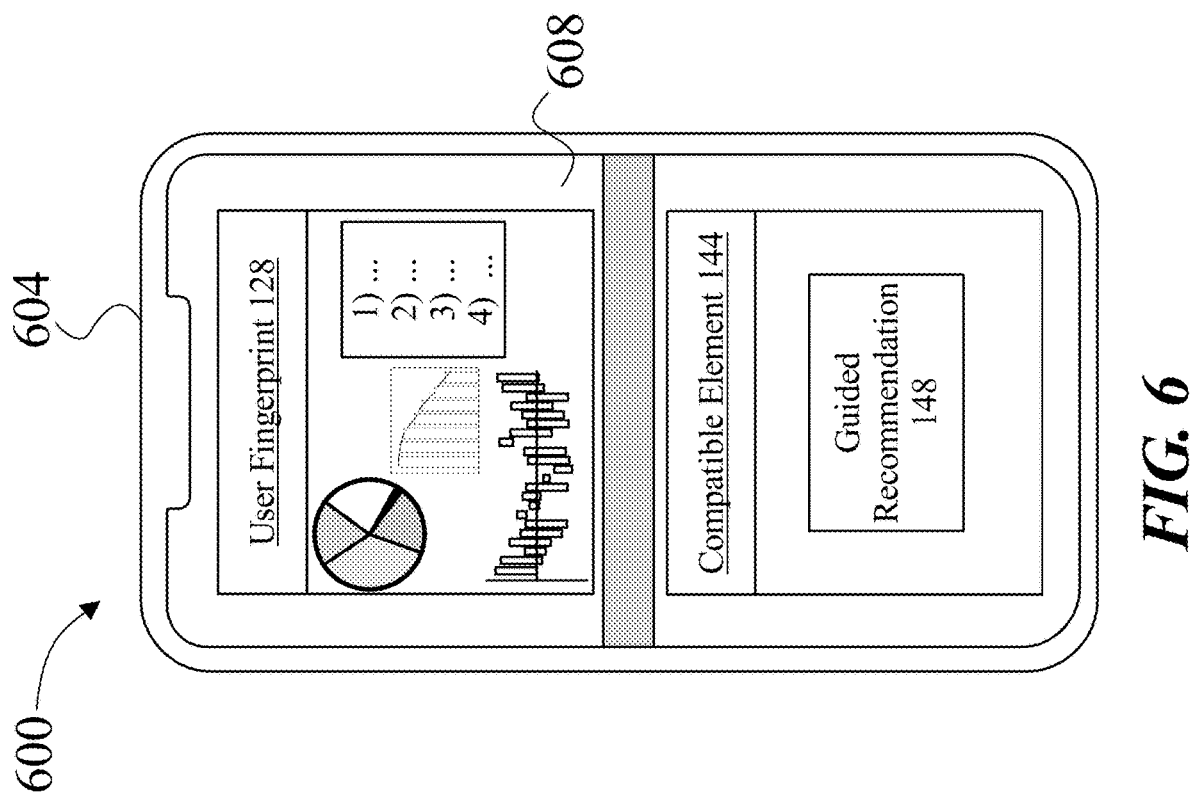
FIG. 6 is a diagrammatic representation illustrating a non-limiting exemplary embodiment of a user device.

Referring now to FIG. 6, a non-limiting exemplary embodiment 600 of a user device 604 is illustrated. Computing device 104 may include user device 604. User device 604 may include representation of the graphical user interface 608, as described herein. Graphical user interface 608 may include a representation of any determination by system 100, for instance and without limitation, data present in user fingerprint 128, include graphics, metrics, and the like. User device 604 may generate a representation of compatible element 144, including a guided recommendation 148 using the graphical user interface 608.

Figure 7:
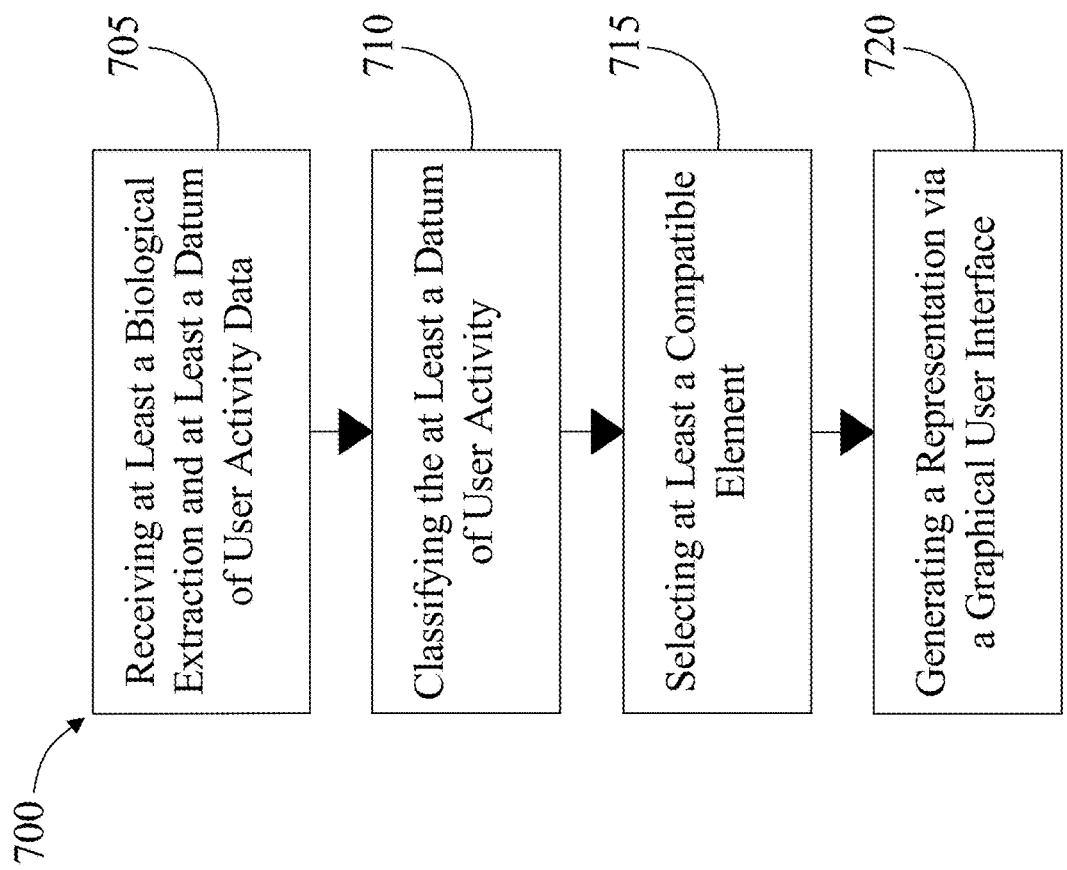
FIG. 7 is a flow diagram illustrating an exemplary workflow of a method for arranging and displaying guided recommendations using a graphical user interface based on biological extraction.

Referring not to FIG. 7, an exemplary embodiment of a method 700 for arranging and displaying guided recommendations using a graphical user interface based on biological extraction is illustrated. At step 705, computing device 104 is configured for receiving, from a wearable device located at a user, at least a biological extraction 108 and at least a datum of user activity data 112. User activity data 112 may include data collected via user input through a graphical user interface. Receiving, from a wearable device located at a user, at least a biological extraction 108 and at least a datum of user activity data 112 may include generating, using the wearable device data, a first training set including a plurality of first data entries including at least an element of wearable device data correlated to at least an element of biological extraction. Receiving at least a biological extraction 108 may include training a label machine-learning model 120 using training data 116, wherein training data 116 includes a plurality of data entries, each data entry of the plurality of data entries including at least an element of biological extraction 108 data correlated to a user function, and generating, using the label machine-learning model 120, a compatibility label 124; this may be implemented, without limitation, as described above in reference to FIGS. 1-6.

Continuing in reference to FIG. 7, at step 710, computing device 104 is configured for classifying the at least a datum of user activity as a function of at least a datum of a user fingerprint 128. Classifying the at least a datum of user activity may include using a classification machine-learning process 132 to generate a classifier 136 which describes a subset of diagnostic outputs 140, wherein the diagnostic output 140 is a subset of user activity data 112 as a function of past user data contained in the user fingerprint 128; this may be implemented, without limitation, as described above in reference to FIGS. 1-6.

Continuing in reference to FIG. 7, at step 715, computing device 104 is configured for selecting at least a compatible element 144 as a function of the training data 116 and the user fingerprint 128, wherein the compatible element 144 comprises a guided recommendation 148. Selecting a compatible element 144 may include using an element machine-learning process 152 to select the compatible element 144 as a function of the classifier 136. Selecting a compatible element 144 using the element machine-learning process 152 may include generating the guided recommendation 148. Selecting the compatible element 144 may include using the element machine-learning process 152 to filter the guided recommendation 148 as a function the user fingerprint 128. Selecting the compatible element 144 as a function of filtering the guided recommendation 148 may include ranking, using a ranking machine learning process 160, guided recommendations 148 as a function of a compatibility index 156; this may be implemented, without limitation, as described above in reference to FIGS. 1-6.

Continuing in reference to FIG. 7, at step 720, computing device 104 is configured for generating a representation using a graphical user interface of the compatible element 144. Generating a representation using a graphical user interface of the compatible label 144 may include updating the graphical user interface display as a function of the compatibility index 156; this may be implemented, without limitation, as described above in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
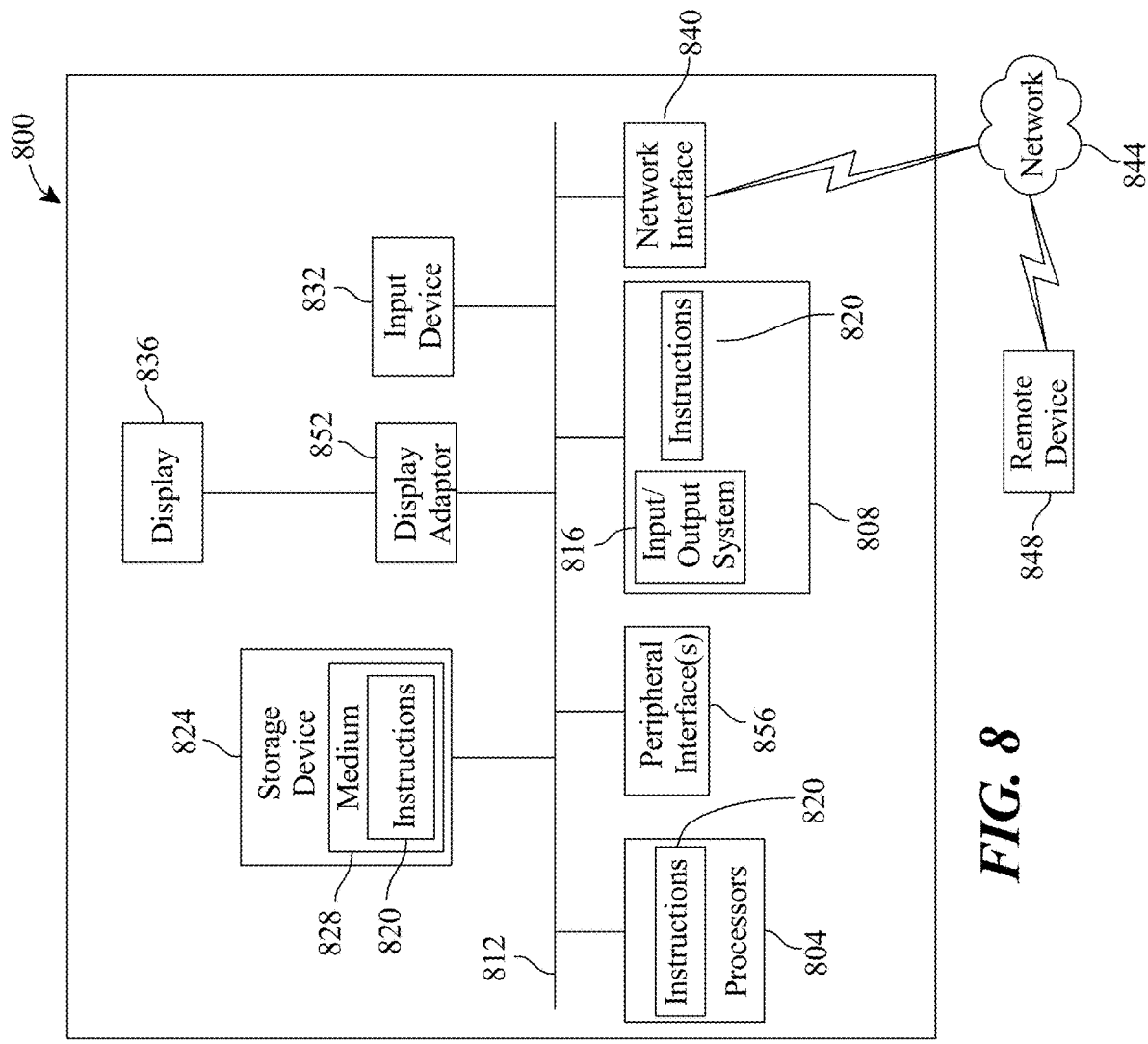
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for displaying ordered compatible elements, the system comprising:
   a computing device, wherein the computing device is configured to:
   receive biological extraction data;
   receive at least a datum of user activity data, wherein the user activity data comprises a plurality of recent online purchases of a user;
   classify the biological extraction data and the at least a datum of the user activity data to at least a user fingerprint;
   select a plurality of compatible elements as a function of the at least a user fingerprint, wherein each of the plurality of compatible elements comprises a guided recommendation;
   order each compatible element of the plurality of compatible elements as a function of a compatibility index; and
   display a representation of the ordered compatible elements using a graphical user interface.

2. The system of claim 1, wherein the biological extraction data is generated by a wearable device located at the user.

3. The system of claim 1, wherein the compatibility index represents a threshold value for the ordered compatible elements to be displayed.

4. The system of claim 1, wherein the computing device is further configured to generate a diagnostic output as a function of the classification of the biological extraction data and the at least a datum of the user activity data to the at least a user fingerprint.

5. The system of claim 1, wherein ordering each compatible element comprises ordering each compatible element of the plurality of compatible elements using a ranking machine learning process.

6. The system of claim 5, wherein ordering each compatible element further comprises ordering each compatible element of the plurality of compatible elements as a function of ranking each of the guided recommendations.

7. The system of claim 1, wherein selecting the plurality of compatible elements comprises selecting the plurality of compatible elements using an element machine learning process.

8. The system of claim 1, wherein the biological extraction data comprises at least a compatibility label.

9. The system of claim 8, wherein the plurality of compatible elements is selected as a function of the compatibility label.

10. The system of claim 1, wherein the user activity data further comprises data received in a user input using the graphical user interface.

11. A method for displaying ordered compatible elements, the method comprising:
- receiving, using a computing device, biological extraction data;
- receiving, at the computing device, at least a datum of user activity data, wherein the user activity data comprises a plurality of recent online purchases of a user;
- classifying, using the computing device, the biological extraction data and the at least a datum of the user activity data to at least a user fingerprint;
- selecting, using the computing device, a plurality of compatible elements as a function of the at least a user fingerprint, wherein each of the plurality of compatible elements comprises a guided recommendation;
- ordering, using the computing device, each compatible element of the plurality of compatible elements as a function of a compatibility index; and
- displaying, using the computing device, a representation of the ordered compatible elements using a graphical user interface.

12. The method of claim 11, wherein the biological extraction data is generated by a wearable device located at the user.

13. The method of claim 11, wherein the compatibility index represents a threshold value for the ordered compatible elements to be displayed.

14. The method of claim 11, wherein the method additionally comprises generating, using the computing device, a diagnostic output as a function of the classification of the biological extraction data and the at least a datum of the user activity data to the at least a user fingerprint.

15. The method of claim 11, wherein ordering each compatible element comprises ordering each compatible element of the plurality of compatible elements using a ranking machine learning process.

16. The method of claim 15, wherein ordering each compatible element further comprises ordering each compatible element of the plurality of compatible elements as a function of ranking each of the guided recommendations.

17. The method of claim 11, wherein selecting the plurality of compatible elements comprises selecting the plurality of compatible elements using an element machine-learning process.

18. The method of claim 11, wherein the biological extraction data comprises at least a compatibility label.

19. The method of claim 18, wherein the plurality of compatible elements is selected as a function of the compatibility label.

20. The method of claim 11, wherein the user activity data further comprises data received in a user input using the graphical user interface.

* * * * *